(12) United States Patent
Kaufman et al.

(10) Patent No.: US 7,306,339 B2
(45) Date of Patent: Dec. 11, 2007

(54) LASER PROJECTION WITH OBJECT FEATURE DETECTION

(75) Inventors: Steven P. Kaufman, Hooksett, NH (US); Arkady Savikovsky, Burlington, MA (US); Christopher C. Chagaris, Manchester, NH (US); Joel Stave, New Boston, NH (US)

(73) Assignee: Laser Projection Technologies, Inc., Londonderry, NH (US)

( * ) Notice: Subject to any disclaimer, the term of this patent is extended or adjusted under 35 U.S.C. 154(b) by 0 days.

(21) Appl. No.: 11/345,784

(22) Filed: Feb. 1, 2006

(65) Prior Publication Data
US 2006/0170870 A1    Aug. 3, 2006

Related U.S. Application Data

(60) Provisional application No. 60/649,241, filed on Feb. 1, 2005.

(51) Int. Cl.
 *G01B 11/03* (2006.01)
 *G01B 11/14* (2006.01)
 *G03B 21/26* (2006.01)

(52) U.S. Cl. .................. 353/28; 353/122; 356/607

(58) Field of Classification Search .............. 353/11, 353/21, 28, 29, 37, 40, 42, 44, 46, 50, 81, 353/82, 94, 98, 99, 122; 356/121, 122, 601, 356/606–608
See application file for complete search history.

(56) References Cited

U.S. PATENT DOCUMENTS

| | | |
|---|---|---|
| 5,090,804 A | 2/1992 | Wong et al. |
| 5,196,900 A | 3/1993 | Pettersen |
| 5,341,183 A | 8/1994 | Dorsey-Palmateer |
| 5,381,258 A | 1/1995 | Bordignon et al. |
| 5,416,591 A | 5/1995 | Yoshimura et al. |
| 5,436,027 A | 7/1995 | Offer |
| 5,450,147 A * | 9/1995 | Dorsey-Palmateer ......... 353/28 |
| 5,559,334 A | 9/1996 | Gupta et al. |

(Continued)

FOREIGN PATENT DOCUMENTS

DE    3301 494 A1    7/1984

(Continued)

*Primary Examiner*—Andrew T Sever
(74) *Attorney, Agent, or Firm*—Peter J. Manus; Edwards Angell Palmer & Dodge LLP

(57) ABSTRACT

A laser projection system scans an output laser light beam onto an object to detect features. A high-sensitivity optical feedback system receives and detects a feedback beam of the output beam light diffusely reflected from the object. The feedback light and projected output beam share the same beam path between beam-steering mirrors of the projector and the object. The laser projection system has light suppression components to control stray scattered light, including ambient light, from being detected. A computer of the laser projection system calculates fiducial points on the object from detected features to align the projection system with the object without using targets. This feature detection is used in a process to guide assembly and fabrication on or to the object, and to verify the accurate placement of parts and fabrication steps in place after they are assembled or processed. In one form, the detected feature is a light spot on the object produced by a second light source.

26 Claims, 13 Drawing Sheets

Fig. 1

U.S. PATENT DOCUMENTS

| | | | |
|---|---|---|---|
| 5,615,013 A | 3/1997 | Rueb et al. | |
| 5,646,859 A | 7/1997 | Petta et al. | |
| 5,663,795 A | 9/1997 | Rueb | |
| 5,671,053 A | 9/1997 | Wigg et al. | |
| 5,889,582 A | 3/1999 | Wong et al. | |
| 5,894,123 A * | 4/1999 | Ohtomo et al. | 250/236 |
| 5,957,559 A | 9/1999 | Rueb et al. | |
| 5,988,862 A | 11/1999 | Kacyra et al. | |
| 6,024,449 A | 2/2000 | Smith | |
| 6,036,319 A | 3/2000 | Rueb et al. | |
| 6,044,170 A | 3/2000 | Migdal et al. | |
| 6,066,845 A | 5/2000 | Rueb et al. | |
| 6,246,468 B1 | 6/2001 | Dimsdale | |
| 6,304,680 B1 | 10/2001 | Blake et al. | |
| 6,365,221 B1 | 4/2002 | Morton | |
| 6,547,397 B1 * | 4/2003 | Kaufman et al. | 353/28 |
| 6,935,748 B2 | 8/2005 | Kaufman et al. | |
| 2004/0189944 A1 | 9/2004 | Kaufman et al. | |
| 2005/0007562 A1 * | 1/2005 | Seki et al. | 353/98 |
| 2005/0035943 A1 * | 2/2005 | Kojima | 345/156 |
| 2005/0082262 A1 | 4/2005 | Rueb et al. | |
| 2005/0121422 A1 | 6/2005 | Morden et al. | |

FOREIGN PATENT DOCUMENTS

| | | |
|---|---|---|
| EP | 1 288 754 A2 | 3/2003 |

* cited by examiner

LASER PROJECTION WITH OBJECT FEATURE DETECTION

CROSS-REFERENCE TO RELATED APPLICATIONS

This application claims priority under 35 USC 119(e) of U.S. Provisional Patent Application No. 60/649,241 filed on Feb. 1, 2005, the disclosure of which is incorporated herein by reference.

FIELD OF THE INVENTION

This invention relates to laser projection systems, and in particular to a laser projection system that projects a glowing template light pattern on an object without requiring retro-reflective or cooperative targets. This invention also relates to a targetless method of producing a glowing template to guide assembly, and a targetless method of assembly to verify the locations of parts after they are assembled or of other fabrication steps.

BACKGROUND OF THE INVENTION

Laser projectors are widely used in manufacturing processes to assist in precision assembly of large scale structures, composite articles, etc. in aerospace, construction and other industries. Laser projectors are distinguished from digitizing scanners. U.S. Pat. No. 6,246,468 to Dimsdale is one example of a laser scanner that uses pulsed laser light to determine range to points on an object and create a point cloud of image data points In the Dimsdale system, a separate video system gathers information about the intensity of the reflected light.

Known laser projectors use a scanned output beam of a continuous wave laser to generate glowing templates on a 3D object surface utilizing computer assisted design (CAD) data for projection trajectories. Typically laser projectors include optical feedback to assist in defining projector's location and orientation in 3D space with respect to the object's coordinate system. This defining is commonly termed "bucking in." It requires use of several, typically three to six, reference (fiducial) points selected or placed on or about the work surface of the object. One specific example of this type of laser projector, for example, is disclosed in U.S. Pat. No. 5,450,147 to Palmateer. The '147 laser projector system uses a plurality of cooperative reference targets mounted, on or adjacent to, the object. These targets return the laser light back into the projector's beam steering system. Another laser projector disclosed in U.S. Pat. No. 5,381,258 to Bordignon specifically requires reference targets to be retro-reflective. Yet another laser projector described in Kaufman and Savikovsky U.S. Pat. No. 6,547,397 issued to two of the present inventors relies on reference targets for both distance ranging and angle measurement.

The requirement to place reference targets onto the object has many practical drawbacks to the process of using laser projectors. It is time and labor consuming. It also degrades precision and reliability due to a lack of precision in the placement and resultant position of the target Some potentially viable applications currently cannot be implemented because they do not allow any target placement on the object surface.

The main reason retro-reflective reference targets are used in almost all laser projecting systems is because they provide quite distinguishable optical feedback signal by returning a substantial portion of projected laser light back into the beam path through the beam steering system.

The maximum output laser beam power allowed for laser projectors due to laser safety regulations is 5 milliwatts. The power of the portion of the laser light that is reflected from a typical retro-reflective target and directed back through the beam steering system is typically about 200 to 1,000 nanowatts depending on the distance between projector and a target and on the size of the beam steering mirrors.

A number of solutions are proposed in the prior art to deal with the problem of the optical feedback using the same beam path through the beam steering system as the output projector beam. They involve different ways to separate the output laser beam from the received feedback light in the laser projector. The aforementioned Palmateer '147 patent utilizes a beam splitter. The Bordignon '258 patent teaches using a particular wedge-shaped lens with a central opening for the output beam. Laser projectors in Kaufman and Savikovsky '397 patent use a reflective optical pick-up prism. Each of these solutions provides somewhat different effectiveness of utilizing received feedback light that is directed toward a photo detector. Using retro-reflective targets and these known solutions to the problems of a shared optical path, typical optical feedback beams that reaches the photo detector are estimated at 50 to 500 nanowatts of power.

It is very desirable in laser projection to use the object features (e.g., corners, holes, fasteners, etc.) as fiducial points for laser projection instead of separately placed retro-reflective targets. However, prior attempts to solve this problem have not provided a solution without other drawbacks. For example, U.S. Pat. No. 5,615,013 to Rueb offers a solution combining a galvanometer and a camera system. A serious drawback of the Rueb arrangement is the existence of two different optical paths for laser projection and camera imaging, which necessitates for frequent mutual calibration between the camera imaging system and the laser projection system. It is necessary to use separate reference targets in the process of this mutual calibration. As a result, the suggested solution reduced accuracy.

In order to maintain a high level of laser projection precision (e.g. to within ±0.015 inch at a laser-to-object distance of 15 feet), it is required that the beam path through the beam steering system is the same for both the optical feedback and the output projector beam. However, if retro-reflective targets are not used, the power level of light diffusely reflected back from a typical object material like plastic or painted metal, and returned through the projector beam steering system, has been determined to be about 1,000 times less than the reflected light power from a typical retro-reflective target. That means the typical optical feedback beam that reaches a photo detector is roughly in the range of 50 to 500 picowatts of power. In other words, the typical optical feedback beam power from the non-target object feature that reaches the photo detector is about 100 million times less than the output laser projector beam power. Because the output beam has to share the optical path with the feedback beam it adds prevailing, unwanted background light due to the light scatter and secondary reflections. This unwanted "stray" light renders the optical feedback signal undistinguishable.

To date, no prior art laser projector that has been able to overcome this problem, that is, to distinguish very weak optical feedback signal in the presence of the powerful output projection beam and ambient light.

In a conventional laser projection application for product assembly, once all the known fiducial points have been detected, a laser projector's computer runs mathematical algorithm to calculate precise position and orientation of the laser projector with respect to the object. Then it starts actual projection. It generates a series of beam steering commands in a precisely arranged way to direct the beam at each given moment of time exactly toward the given trajectory CAD point (x, y, z) on the surface of the 3D object. The beam strikes the surface of the object following the computer-controlled trajectory in a repetitive manner. With sufficiently high beam speed, the trajectory of the projected beam on the object's surface appears to human eye as a continuous glowing line.

Glowing templates generated by laser projection are used in production assembly processes to assist in the precise positioning of parts, components, and the like on any flat or curvilinear surfaces. Presently laser projection technology is widely used in manufacturing of composite parts, in aircraft and marine industries, or other large machinery assembly processes, truss building, and other applications. It gives the user ability to eliminate expensive hard tools, jigs, templates, and fixtures. It also brings flexibility and full CAD compatibility into the assembly process.

In the laser assisted assembly process, a user positions component parts by aligning some features (edges, corners, etc.) of a part with the glowing template. After the part positioning is completed, the user fixes the part with respect to the article being assembled. The person assembling the article uses his or her eyesight to make a judgment about proper alignment of the part to the glowing template. Because this process relies on the visual judgment of a worker, it is subjective, and its quality may be substantially reduced by human errors.

Human errors adversely impact any manufacturing process, they are unacceptable, and they have to be revealed as soon as possible. In aircraft manufacturing, for example, every production step has to be verified and properly documented. One hundred percent quality assurance is often required. Therefore, a device and method that combines the capabilities of laser projection with immediate verification of part placement during assembly process are very desirable. They would provide the benefits of revealing and fixing human errors right on the spot, thus avoiding very costly and time-consuming off-line testing procedures.

It is therefore a principal object of this invention to provide a laser projector that distinguishes very weak optical feedback signal returned from any object surface in the presence of the relatively powerful output projector beam and the ambient light.

A further object of this invention is to provide such a laser projector with high sensitivity optical feedback sufficient to enable scanning of object features as fiducial points.

Another aspect of this invention is to provide a method of using glowing light templates in production assembly processes without retro-reflective targets at every necessary fiducial point.

Still another object of the invention is to provide a method of immediate, in-place verification of the proper assembly of a part or other fabrication processing steps.

SUMMARY OF THE INVENTION

A laser projector with a high-sensitivity optical feedback from a scanned object shares the beam path of the laser output beam through the beam steering system to the object with the output projecting beam. The laser projector separates the output beam and the optical feedback beam while substantially suppressing unwanted prevailing background light, including the ambient light illuminating the object, from reaching a photodetector for the feedback beam. This separation makes the weak optical feedback signal from a typical object feature distinguishable enough to enable usage of object features as fiducial points for laser projection, thereby providing a targetless laser projection.

The laser projector has a computer that converts the optical feedback scan signal from the photodetector into a digital image. It processes the image to determine object features locations with respect to the projector coordinate system. The laser projector computer also defines the projector location and orientation in 3D space with respect to the object based on the optical feedback scan data form the object's features.

This laser projector can scan different object features, such as corners, holes or other fabricated features, edges, and fasteners, and obtain spatial coordinates of those features with respect to projector's coordinate system. The projector uses 3D CAD data for the features and their obtained spatial coordinates to accurately determine its location and orientation in 3D space with respect to the object's coordinate system prior to performing actual projection. While in essence a targetless system, as needed, the projector can also scan retro-reflective cooperative targets mounted on the object, as one type of the object features. In one form of this invention, the detected feature is a light spot on the object, e.g. one projected from a separate laser light source.

Viewed as an apparatus, the present invention provides a laser projection system with feature detection on the surface of an object, using a laser projector that projects a laser light beam onto the surface along a beam path and scans the output beam to form a glowing template on the surface. A portion of the output light is reflected from the surface back to said projector as a feedback light beam. An optical detector at the projector that receives said feedback light beam and converts it into an electrical image signal that corresponds to the intensity of the detected feedback light. A suppression system that controls stray light other than said feedback light to prevent it from reaching the optical detector. The projected light beam and said feedback light beam are associated with a given point on the surface and propagate in opposite directions along the same beam path.

The invention also includes a method of generating a glowing template on an object for precision placement of component parts in 3D space. This method scans a glowing template on object features to create a tool data set of reference or fiducial points to buck (align) the laser projector with the object coordinate system prior to performing actual projection on the object to guide the assembly. The process of this invention further includes a method for assembling with precision placement component parts in 3D space, onto and/or supported by an object. In one form, the process includes projecting a laser light beam onto the object, selecting features on the object before assembly, the selecting including projecting a glowing template scan box around a selected feature, scanning the glowing template within the scan box, detecting light reflected back from the object along the scanned laser light beam, suppressing all light from entering the detector except for the feedback light, determining a digital image of the feature from the detected feedback light, and calculating a fiducial point from the feature. The reflected light is diffusely reflected from the object. The process further includes calculating from plural fiducial points on the object the relative position and orientation of the source of said projecting and the object, and projecting a glowing template on the object that guides the assembly of the parts to or processing of fabrication steps on the object.

The invention also includes a method of assembly a structure in 3D space with verification of the placement of component assembled parts and fabrication process steps on the object. The assembly process includes steps of generating glowing templates, placing component parts in 3D space, and verifying real locations of placed component parts against nominal design parameters by scanning their features. More specifically, this process includes providing a laser projector with high-sensitivity optical feedback capable of scanning features of a part and/or fabrication processing step after it has been positioned during the assembly and/or fabrication of an article to convert the optical feedback scan signal into a digital image, image processing to determine the part or fabricaction features locations with respect to projector's coordinate system, and computing to verify the location of the placed part and/or fabrication with respect to nominal (e.g., CAD) design parameters.

These and other features and objects of the invention will be more fully understood from the following detailed description of the invention which should be read in light of the accompanying drawings.

DETAILED DESCRIPTION OF THE INVENTION

Figure 1:
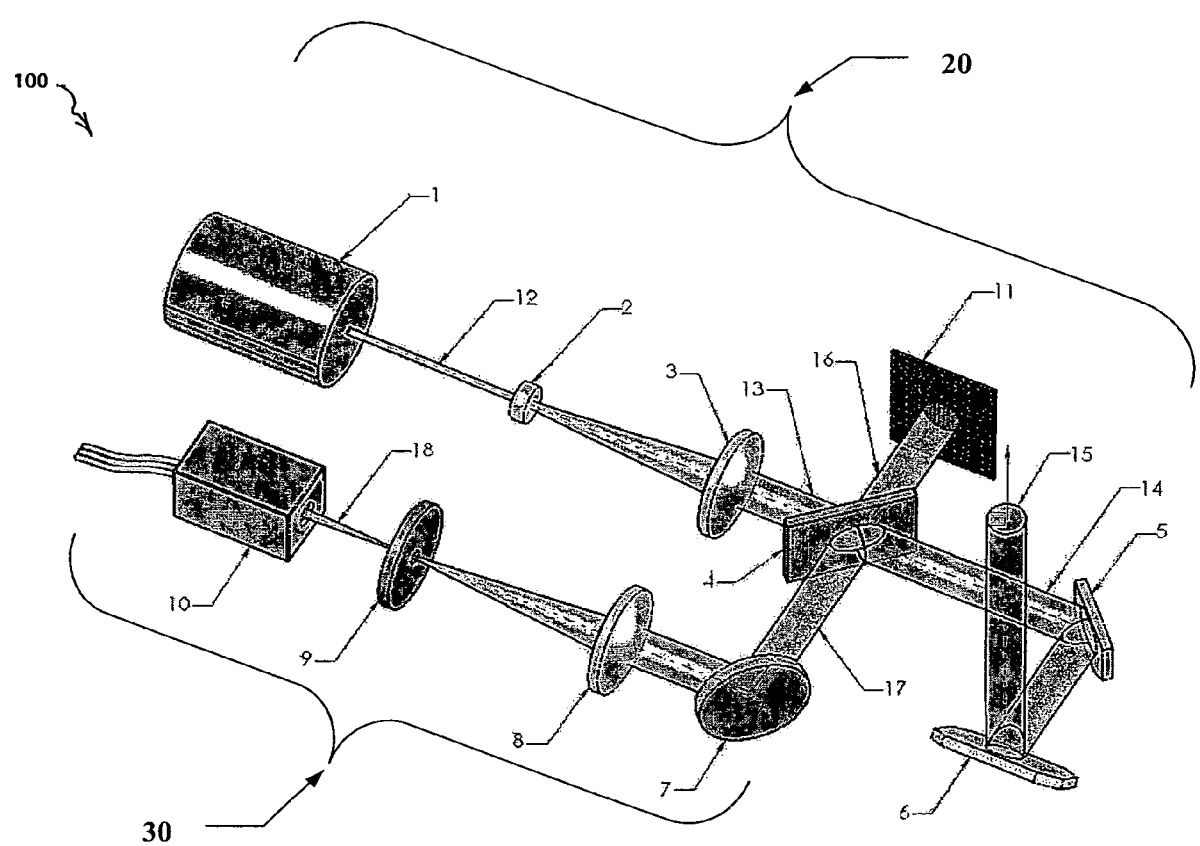
FIG. 1 is a simplified view in perspective of a laser projector according to the present invention.

FIG. 1 shows a targetless laser projector ("TLP") 20 according to the present invention. The TLP 20 has two major optical subsystems—a projection subsystem 20 and an optical feedback subsystem 30. The projection subsystem 20 includes a laser 1, beam expanding lenses 2 and 3, a beam splitter 4, a beam dump 11, and beam steering mirrors 5 and 6. The beam steering mirrors are mounted on shafts of corresponding galvanometers 203, 204 in FIG. 6, as is well known in the laser projection art. The optical feedback subsystem 30 includes a mirror 7, a focusing lens 8, a spatial filter 9, and a high-sensitivity photo detector 10.

The laser 1 emits a laser beam 12. The laser 1 is typically a solid state diode pumped laser that produces light at the "green" wavelength of 532 nanometers. The power of the beam 12 output by the laser is preferably not more than 5 milliwatts, the upper power limit for class IIIa lasers, and is a continuous wave output. The beam 12 has a typical diameter of about 0.4 to about 1.0 millimeter. Lenses 2 and 3 expand the beam 12 as it goes through them preferably about 10 to 15 times. The combination of lenses 2 and 3 also functions as the beam collimator so that the expanded beam 13 has about 10 to 15 times less divergence than the beam 12. The beam 13 then passes through the beam splitter plate 4 of known design. One part of the beam 13 reflects from the beam splitter 4 shown as beam 16, toward the beam dump 11. Another part of the beam 13 passes through the beam splitter 4 along the same direction as beam 14 directed toward the beam steering mirrors 5 and 6, in that order. The beam 15 that reflects from the second steering mirror 6 is directed toward the object of projection (e.g. object 105 in FIG. 5).

The object is typically a work piece formed of a solid material, a composite of materials, or an assembly of parts and/or materials. In a typical aerospace application, the object is an aircraft, or a part of an aircraft. The object, at least in part, diffusely reflects light. It can, however, strongly reflect light, e.g. from polished or glossy painted surface or surfaces. The object can be a liquid, e.g. as in a wet coating of paint or adhesive. However, the object is normally a solid, is diffusely reflective, and has no retro-reflective targets mounted thereon.

Figure 2:
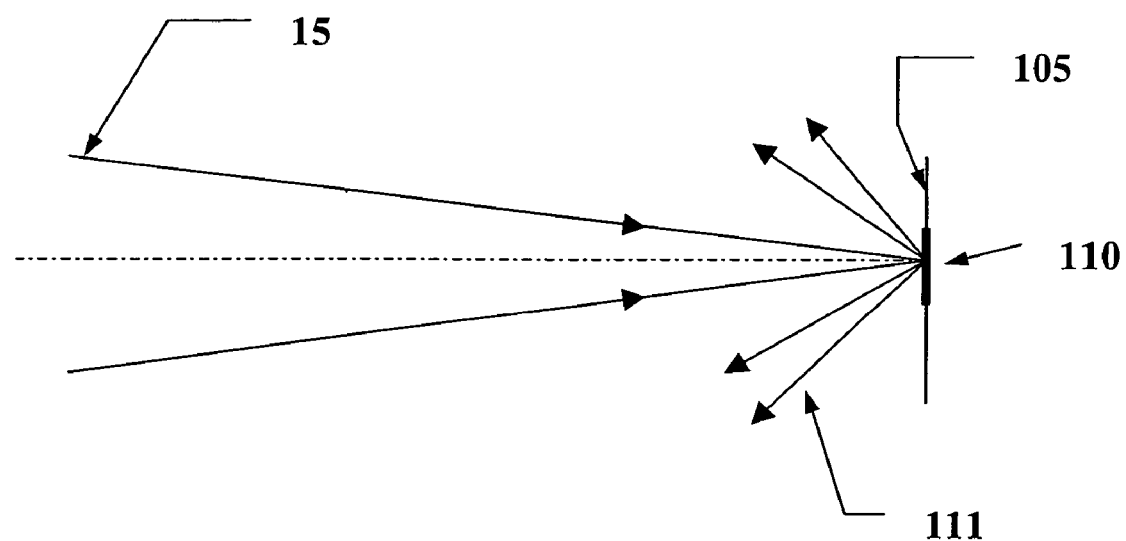
FIG. 2 is a simplified detail view in cross-section of the projected laser beam from the projector shown in FIG. 1 striking the outer surface of an object and being diffusely reflected.

The output beam 15 shown for simplicity in FIG. 1 as a collimated beam. By slight movement of the lens 3 along its optical axis, the output beam 15 can be focused onto the surface of the object. This focusing makes the beam 15 convergent toward its focusing point. FIG. 2 illustrates the focused laser projector beam 15 striking the surface of the object 105 at the focusing spot 110. Generally, the object's surface diffusively reflects the incoming beam 15. Because of diffusion, the reflected light 111 is widely spread back toward laser projector 20. As discussed above, a very small portion of this diffusely reflected light 111 gets back through the beam steering mirrors 5 and 6 into the optical feedback subsystem 30.

The returned portion of the diffusely reflected light 111 makes its way toward the beam splitter 4 sharing the same beam path through mirrors 5 and 6 with the projecting beam 15. This reflected light is also termed herein the feedback beam, although it is not converged into a beam in the same way that lenses 2 and 3 create a projected output beam. Part of the returned reflected light reflects as beam 17 from the beam splitter 4 into the optical feedback subsystem 30. The beam splitter 4 decouples the return feedback light beam from the output beam in their shared beam path. Within subsystem 30, the beam 17 further reflects from mirror 7, and is then focused onto the spatial filter 9. The beam 18 transmitted through spatial filter 9 finally enters the high-sensitivity photo detector 10 where it is converted into an electrical signal that corresponds to the intensity of the feedback beam 18.

Typically beam splitter 4 has a transmission-to-reflection ratio from 50:50 to 90:10. The preferred ratio for the present invention is 90:10 because it is characterized by less beam power loss for the laser projection.

The power level of light diffusely reflected back from a typical object material such as plastic or painted metal, returned through the projector's beam steering system, and reflected from beam splitter 4 as the beam 17, is in the range of about 50 to about 500 picowatts of power. The high-sensitivity photo detector 10 can convert such extremely low level of optical power into a corresponding electrical signal. The detector 10 is preferably a photo multiplier tube (PMT).

A substantial problem solved by this invention is the suppression of excessive (also termed herein "unwanted" or "stray") background light that otherwise makes the optical feedback signal from diffusely reflected surface of the object 105 indistinguishable. Major sources of the excessive background light that enters the feedback subsystem 30 along with the feedback beam 17 include:

1) Part of the beam 16 that diffusely reflects from the beam dump 11 and passes through the beam splitter 4 back into the subsystem 30;
2) Part of the laser beam 13 scattered from the surface of the beam splitter 4 toward the subsystem 30;
3) Part of the laser beam 14 scattered back from the beam steering mirrors 5 and 6; and
4) Part of ambient light illuminating object 105 that diffusely reflects from the surface, reaches laser projector, passes though the beam steering mirrors 5 and 6, reflects from the beam splitter 4, and gets into the optical feedback subsystem 30.

The beam dump 11 is designed to minimize the unwanted background light reflected from it back into the system. Beam dump 11 is made out of a black material with very low light scattering, for example, Low-Pile Black Velvet available through the McMaster catalog. The distance between the beam dump 11 and the beam splitter 4 is preferably not less than 4 inches. To further reduce reflection back into the system, the beam dump 11 is also preferably tilted by at least 45 degrees with respect to the axis of the beam 16.

Figure 3:
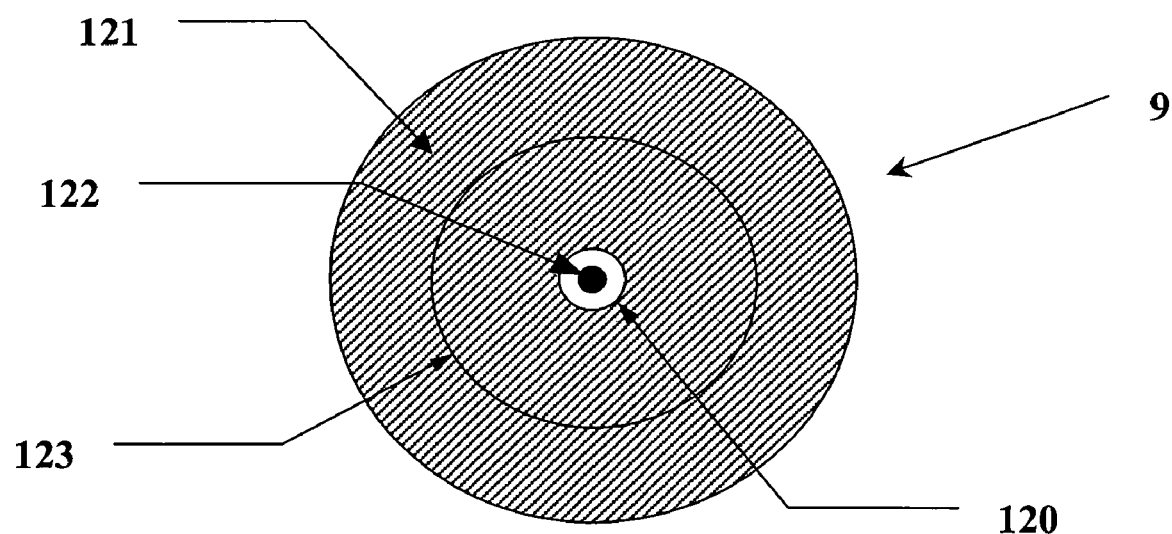
FIG. 3 is a detailed plan view of the spatial filter shown in FIG. 1.

The converging lens 8 and the spatial filter 9 provide further suppression of the unwanted excessive background light while at the same time providing effective transmission of the useful feedback beam. Spatial filter 9 is shown in detail in FIG. 3. It is formed by a pinhole 120 in a disk-shaped mask 121 oriented transversely to the optical axis of the feedback beam 17, 18. The lens 8 images the surface of the object 105 illuminated by the projected light beam 15 back onto the spatial filter 9. The rays of the light 111 diffusely reflected from the focused spot 110 that are collected through the beam steering mirrors 5 and 6 and reflected as beam 17 from the beam splitter 4 will be concentrated by the lens 8 into a "point" 122 on the spatial filter 9. The real size of this concentrated point image 122 is diffraction limited; it is typically a spot about 15 to 25 micrometers in diameter, for a focused beam spot on the object 105 having a typical diameter, as noted above, of about 0.4 to 1.0 mm. This image stays at the same location 122 on the spatial filter 9 for any position of the spot 110 on the surface of the object 105, e.g. regardless of the beam steering mirrors angles, because the returned optical feedback light shares its optical path with the projecting laser beam 14, 15.

The image 122 of the point 105 is located in the center of the pinhole 120, hence the optical feedback beam 17 concentrated by the lens 8 into the image 22 will go freely through the spatial filter 9 toward the photo detector 10. Because the excessive background light that goes through the lens 8 is not collimated (it is originated from light scattering surfaces) it is not concentrated within the pinhole 120 but rather blurred over the area 123. Therefore, the spatial filter 9 blocks the excessive background light to distinguish the optical feedback signal from the object surface.

The pinhole 120 is aligned on the optical axis of the beam 17, 18 together with the optical axis of the lens 8 on the light entrance to the PMT 10. The diameter of the pinhole 20 is preferably about 4 times the diameter of the feedback beam at the pinhole (point image 122), in the focal plane of the lens 8. For a focused beam diameter of 15 to 25 micrometers, the pinhole is preferably 100 micrometers in diameter. An increase in the pinhole diameter increases the "field of view" of the object, which allows more ambient light incident on the object to enter the subsystem 30 and the PMT 10, thereby degrading the performance of the system. An increase in the pinhole diameter also allows more stray scattered light within the laser projector to reach the PMT, which also degrades the performance of the system. A decrease in the preferred diameter, on the other hand, creates problems in achieving the proper alignment of the components, particularly as the parts heat and there are thermal shifts, or as the lens 3 is moved to refocus the laser output beam 13, e.g. to accommodate different laser-to-object distances.

The mirror 7 further reduces unwanted background signal from the ambient light. The mirror 7 preferably has its reflective surface covered with a layer that reflects only light with the wavelength of laser 1 (532 nanometers in this embodiment). It therefore works as a band pass filter, reducing the background signal originated by the ambient light. Alternatively, a laser wavelength transmission band pass filter can be placed somewhere into the beam within the subsystem 30.

Figure 4:
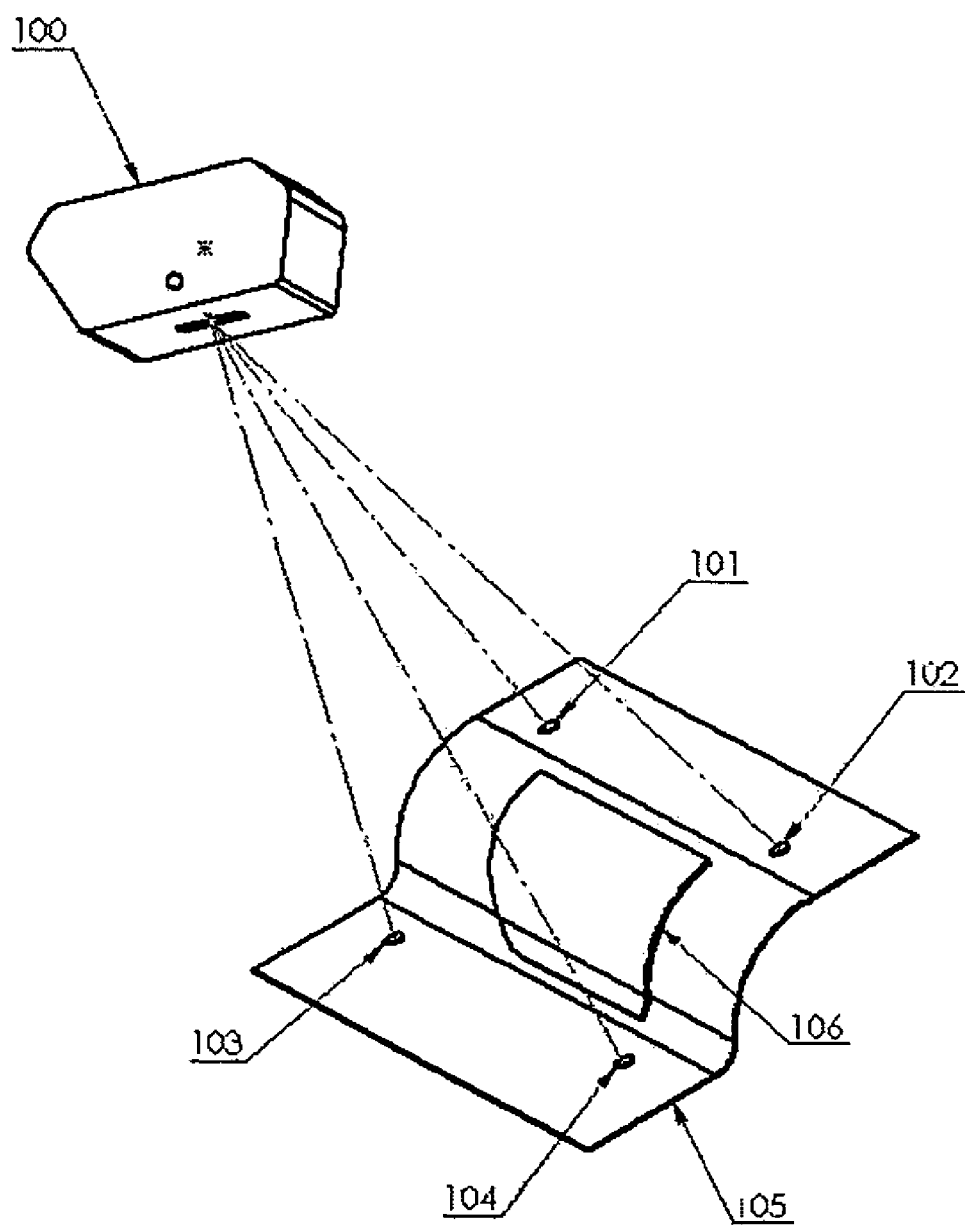
FIG. 4 is a simplified view in perspective of a prior art laser projector scanning a 3D object with retro-reflective targets secured thereon.

FIG. 4 illustrates a prior art method of 3D laser projection—generating a glowing template onto an object for precision placement of component parts in 3D space. Laser projector 100 is arbitrary located in 3D space with respect to the object 105. There are two major steps in this method of laser projection:

Step 1. The laser projector 100 utilizes its optical feedback capabilities and the set of retro-reflective or cooperative targets 101, 102, 103, and 104 as fiducial points to determine projector's location and orientation in 3D space with respect to the object 105. The computation is based on a given set of coordinate data for the targets 101-104 with respect to the object 105. This process referred herein by the phrase "buck into the object's coordinate system".

Step 2. The laser projector utilizes input CAD data for the predetermined projection trajectory for a given object 105 in combination with projector's location data determined in the Step 1. It produces rapidly moving laser beam that strikes the surface of the object 105 precisely following a predetermined, computer controlled trajectory in a repetitive manner. With sufficiently high beam speed and refresh rate, the trajectory of the projected beam on the object appears to human eye as a continuous glowing line 106.

The prior art implementation is well known in the industry. Solutions disclosed in U.S. Patents referred above are different in certain aspects but they all rely on use of reference cooperative or retro-reflective targets as fiducial points for bucking into the object's coordinate system. Typically, at least three to six fiducial points are required.

Figure 5:
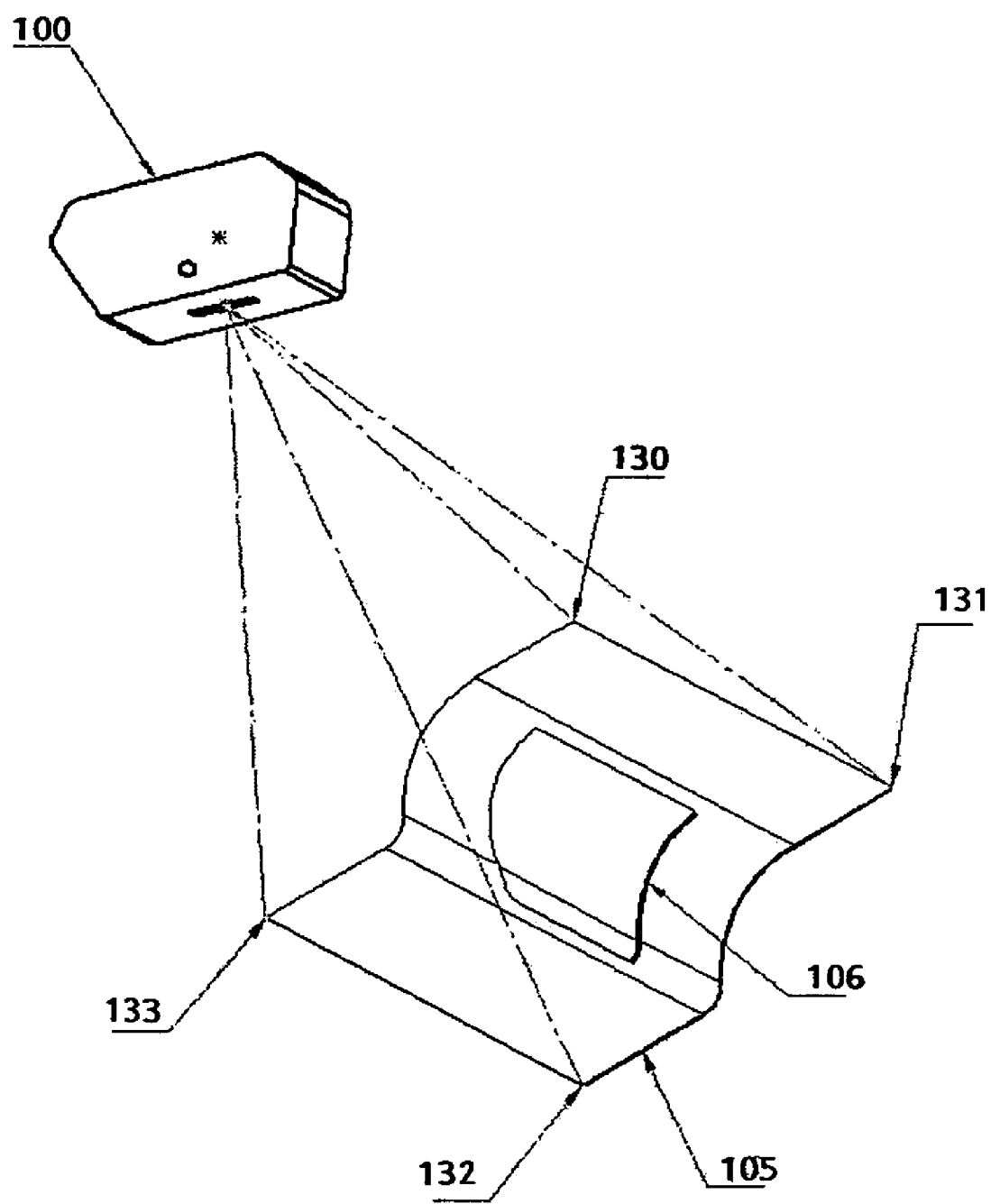
FIG. 5 is a view corresponding to FIG. 4 showing the laser projector of FIG. 1 scanning the same 3D object, but using object feature points as fiducial points according to the present invention.

The targetless method of the present invention is illustrated in FIG. 5. There are two major steps in this method of laser projection.

Step 1. The laser projector 100, using the optical components described above with reference to FIGS. 1-3, and its high sensitivity optical feedback capabilities, together with the image processing and computational features of the invention described below, which together constitute the laser projector "apparatus". It is capable of scanning object features and obtaining distinctive signal from diffusely reflective conventional surfaces. It uses given set of coordinate data for corners 130-133 of to the object 105 as fiducial points to determine location and orientation of the laser projector 100 in 3D space with respect to the object 105.

Step 2. The laser projector 100 utilizes input CAD data for the predetermined projection trajectory for the object 105 in combination with projector's location data determined in the Step 1. It produces rapidly moving laser beam that strikes the surface of the object 105 precisely following a predetermined, computer controlled trajectory in a repetitive manner. With sufficiently high beam speed and refresh rate, the trajectory of the projected beam on the object appears to human eye as a continuous glowing line 106.

Figure 6:
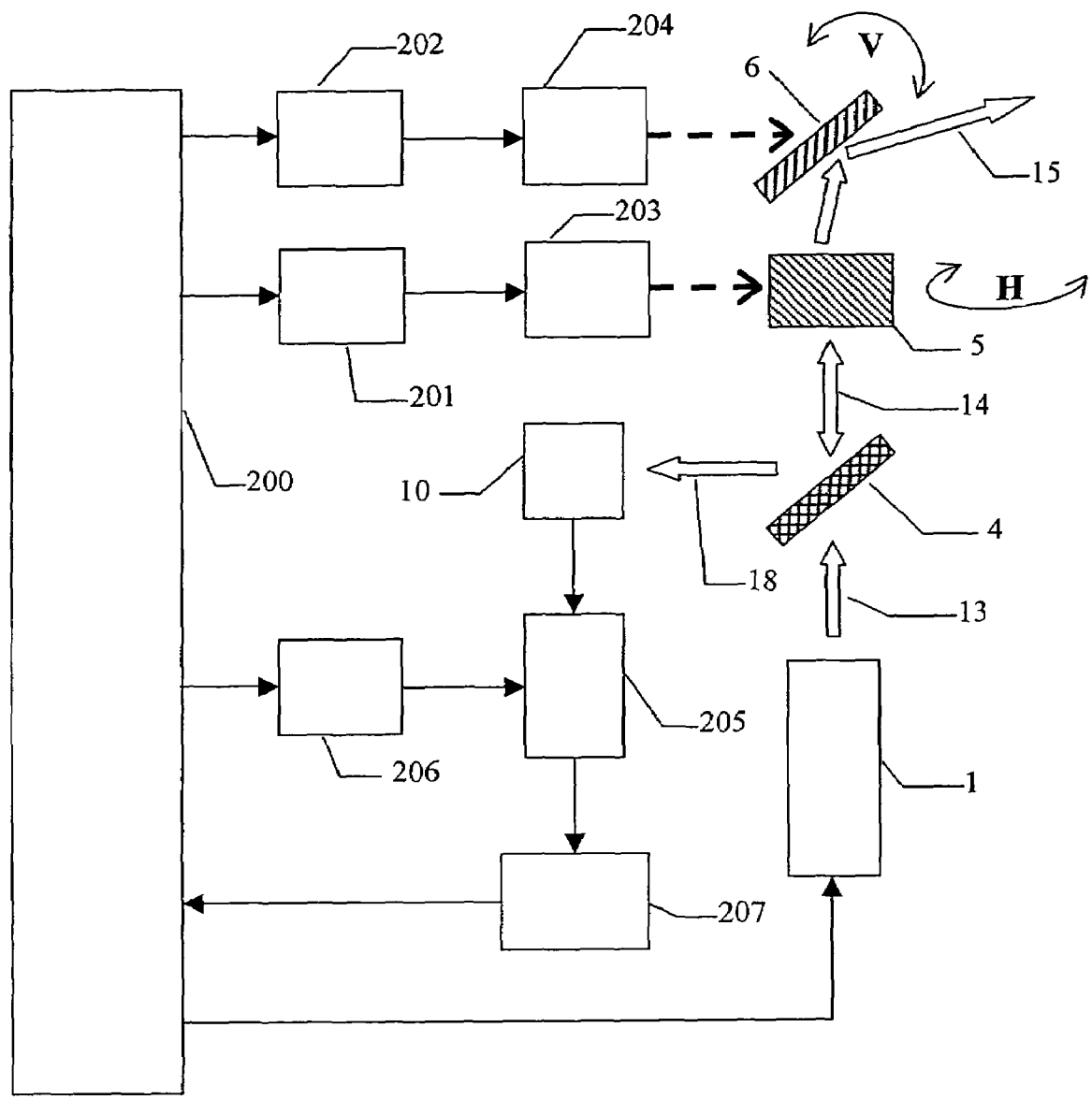
FIG. 6 is a simplified schematic block diagram of the laser projector shown in FIG. 1 illustrating its control and image signal processing electronics.

A functional block diagram of the targetless laser projector 100 of the present invention is shown in FIG. 6.

The projector output beam 15 is being directed toward the object by the pair of orthogonal mirrors 5 and 6 as depicted in FIG. 1. The mirrors 5 and 6 are mounted on the shafts of corresponding galvanometers 203 and 204. The galvanometers are high-precision servo motors containing angular position sensors. Galvanometers that widely used in industrial applications for laser projection are, for example, models 6860 or 6220 made by Cambridge Technology, Inc. Galvanometer 203 rotates mirror 5 to steer the beam 15 in the projector's horizontal (azimuth) plane. The azimuth beam steering angle is denoted as H. Galvanometer 204 rotates mirror 6 to steer the beam 15 in projector's vertical (elevation) plane. The elevation beam steering angle is denoted as V. By steering both mirrors in coordinated manner laser projector can direct output beam toward any point on the object within the angular range of galvanometers. The typical range for H and V angles is ±30 degrees. Galvanometers 203 and 204 are activated by corresponding servo drivers 201 and 202. Each servo driver typically has an integrated 16 bit Digital-to-Analog Converter (DAC) as a front end input interface that obtains command data from a computer 200.

The laser 1 that generates the continuous wave beam 13 is controlled in an ON/OFF mode by the computer 200. This allows the laser projector 100 to generate piece-wise trajectories, or raster scan patterns. As described above, the beam 13 goes through the beam splitter 4. The optical feedback beam 18 from the object 105 via the output beam path, the steering mirrors, and the beam splitter 4, gets onto the high-sensitivity photo detector 10, preferably a photo multiplier tube (PMT).

The output PMT electrical signal goes through an amplifier 205 to the Analog-to-Digital Converter (ADC) 207 to digitize the analog output signal of the amplifier 205. The preferable ADC resolution is 12 to 16 bits. The ADC 207 output is connected to the digital input of the computer 200.

DAC 206 controls the gain of an amplifier 205 to compensate for changes in the PMT signal strength caused by variations in the optical feedback beam reflected from different kinds of object surfaces. Control of the amplifier 205 gain results in the consistent dynamic range for the input signal of ADC 207. While the present invention operates without retro-reflective targets, should the object nevertheless have a retro-reflector on it, the gain adjustment controls the much stronger return beam signal produced by the target.

As noted above, in the first step of the laser projection process, the laser projector is aligned to or "bucks into" the object's coordinate system e.g. to determine its location and orientation in 3D space with respect to the object. This is accomplished using a set of reference (fiducial) points. The (x, y, z) coordinates of the reference points are known with respect to the object coordinate system, and they are entered into the memory of the computer 200 as an input data set. This data set will be referred further in this text as the "Tool Data Set," the conventional term in the industry.

In other words, Tool Data Set is a list of coordinates for the reference points:

Reference Point 1: x1, y1, z1;
Reference Point 2: x2, y2, z2;
Reference Point 3: x3, y3, z3;
Reference Point 4: x4, y4, z4;
Reference Point 5: x5, y5, z5;
Reference Point 6: x6, y6, z6;
 . . . [Etc.]. . .

In this invention, selected object features are used as the reference (or fiducial) points. Object features include sharp and rounded corners, holes, fasteners, "crosses," and the like. For example, FIG. 5 shows use of the sharp corners 130-133 of the object 105 as reference points. To be more specific, each corner vertex is assigned as a reference point, so the Tool Data Set for the case depicted in FIG. 5 includes coordinates of the corners' vertices:

Corner 130: x1, y1, z1;
Corner 131: x2, y2, z2;
Corner 132: x3, y3, z3;
Corner 133: x4, y4, z4;

If corners are rounded, lines can be computed from edge-detected "shoulder" portions of the corner that are extended computationally to a "virtual" corner meeting point in space that serves as the one reference point for this rounded corner feature. For holes in the object, edge detection and computation can produce a like "virtual" reference point at the calculated center of the hole, e.g. a drilled cylindrical hole.

Figure 7:
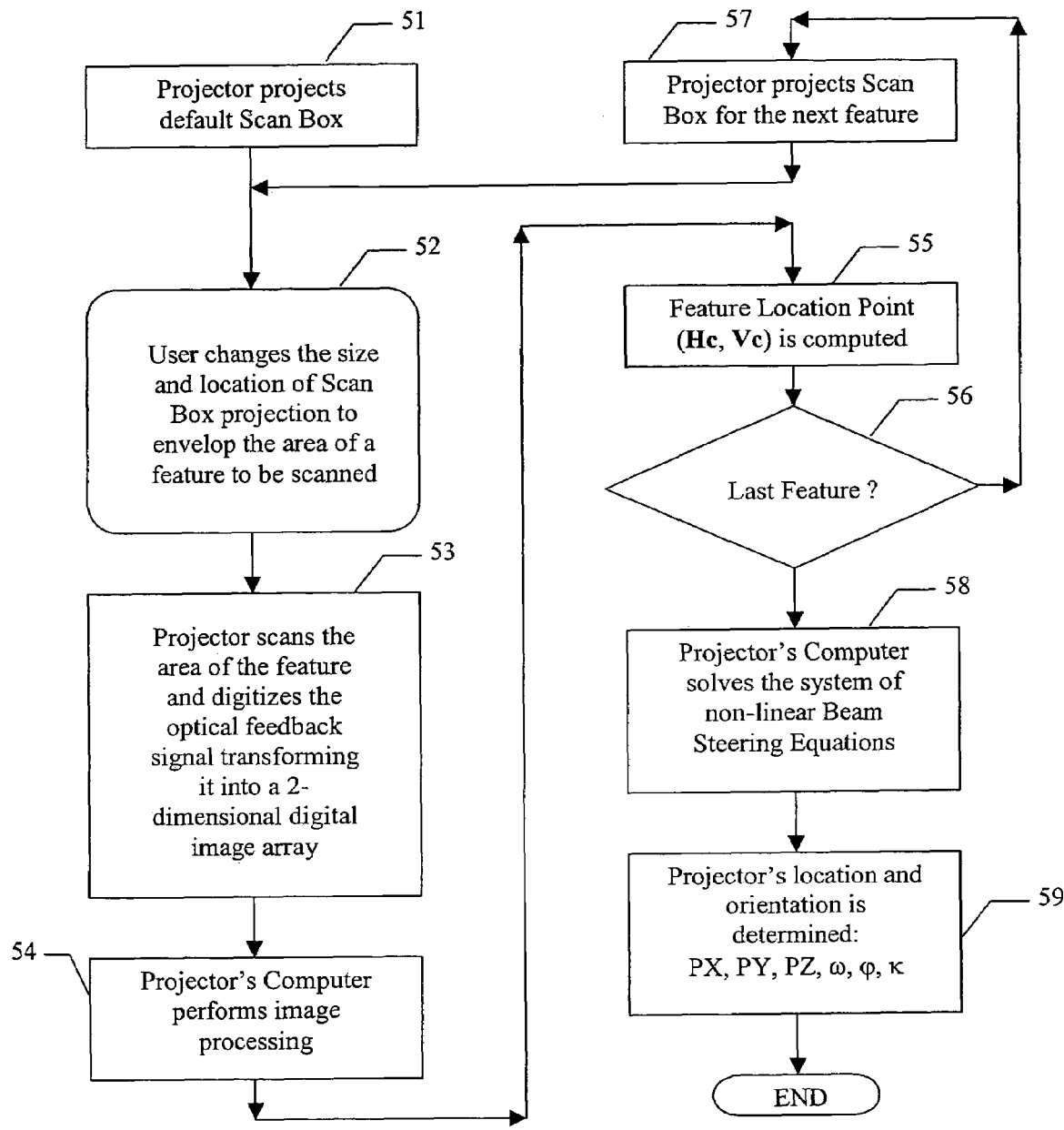
FIG. 7 is a flow chart of the control and processing functions performed by the computer of the laser projector shown in FIGS. 1 and 6 to buck the projector into the coordinate system of the object.
Figure 8:
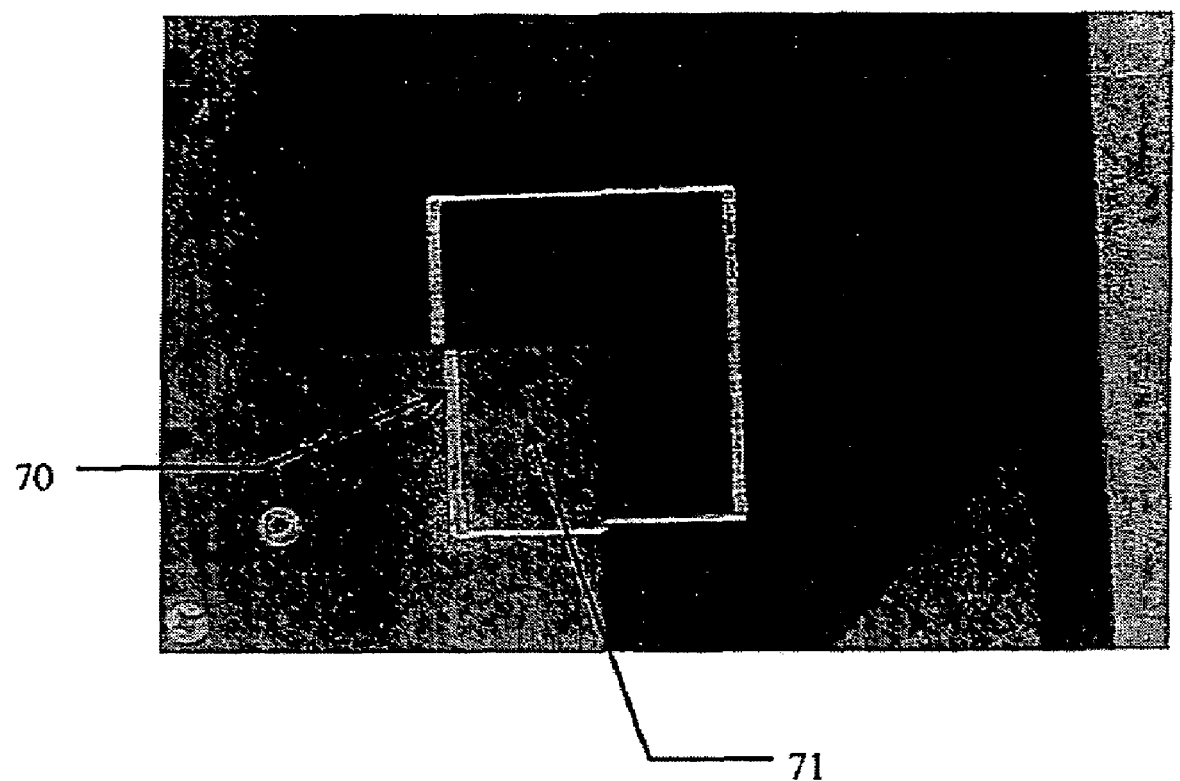
FIG. 8 is an image of a typical object with a scan box projected onto and enclosing an object feature point, a corner.

FIG. 7 shows an algorithm according to the present invention for the laser projector "bucking into" the object coordinate system using object features as reference points. At step 51 the projector creates a glowing template referring here as a "scan box". The scan box outlines a rectangular area on the surface of the object were the feature scan will occur. The scan box projected at step 51 has a default location, preferably, in the center of the beam steering range (both, in azimuth and elevation) and a default size, for example, 0.5×0.5 degrees corresponding to approximately 1.5×1.5 inches at 15 feet distance. At step 52 the user changes the size and location of the scan box projected on the surface of the object to enclose the area of the feature needed to be scanned. To control the scan box, the user operates the laser projector through its computer 200 using keyboard or mouse input interface. An example of a typical scan box 70 is shown in FIG. 8. Scan box 70 envelops the area around the feature 71, which has a shape of a corner.

Figure 9:
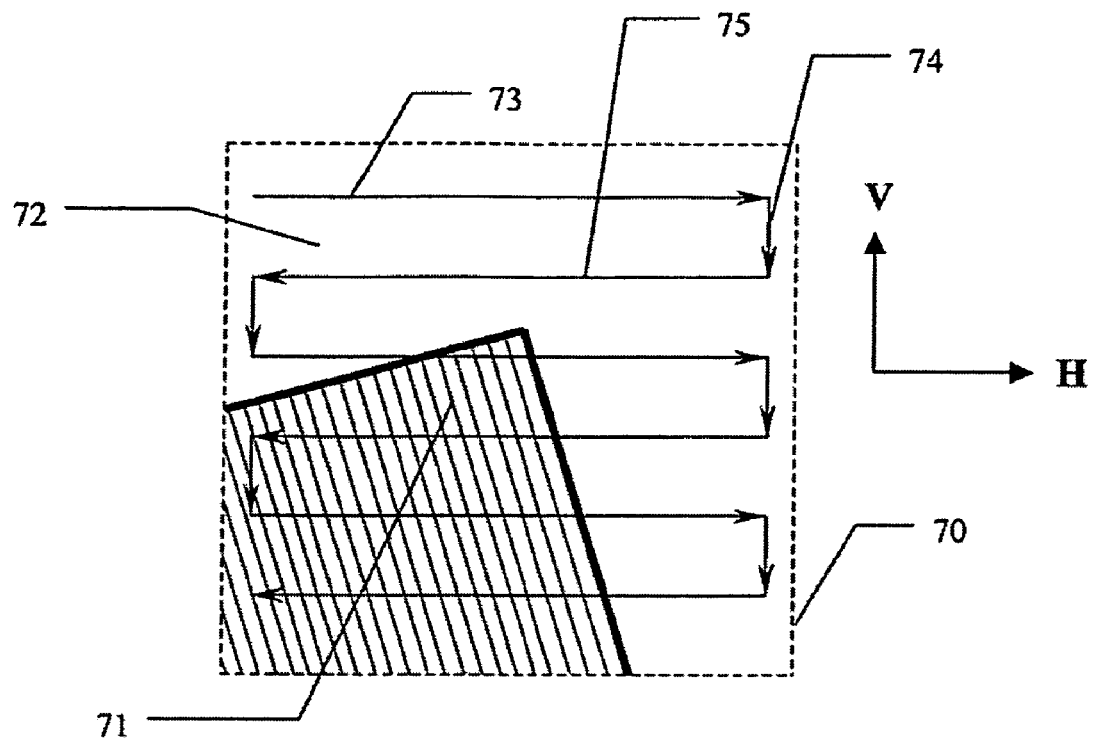
FIGS. 9 and 10 are diagrams showing alternating raster scan patterns and associated scan boxes on an object according to the present invention.

At step 53 projector scans the area of the feature and digitizes the optical feedback signal transforming it into a 2-dimensional digital image array. The preferred scanning method in this invention is raster scanning. The computer 200 generates a scan trajectory as a series of beam steering commands at equal time increments sent to DACs 201 and 202. In the presently preferred implementation of this invention, the feature scan uses a preliminary scan and final scan. Both preliminary and final scans are bi-directional but with different scanning patterns shown schematically in FIGS. 9 and 10, respectively. The preliminary scan of FIG. 9 starts first, and follows the scan pattern 72. The goal of preliminary scan is to determine the optical feedback signal amplitude, and to set up proper gain for amplifier 205 through DAC 206.

Figure 11:
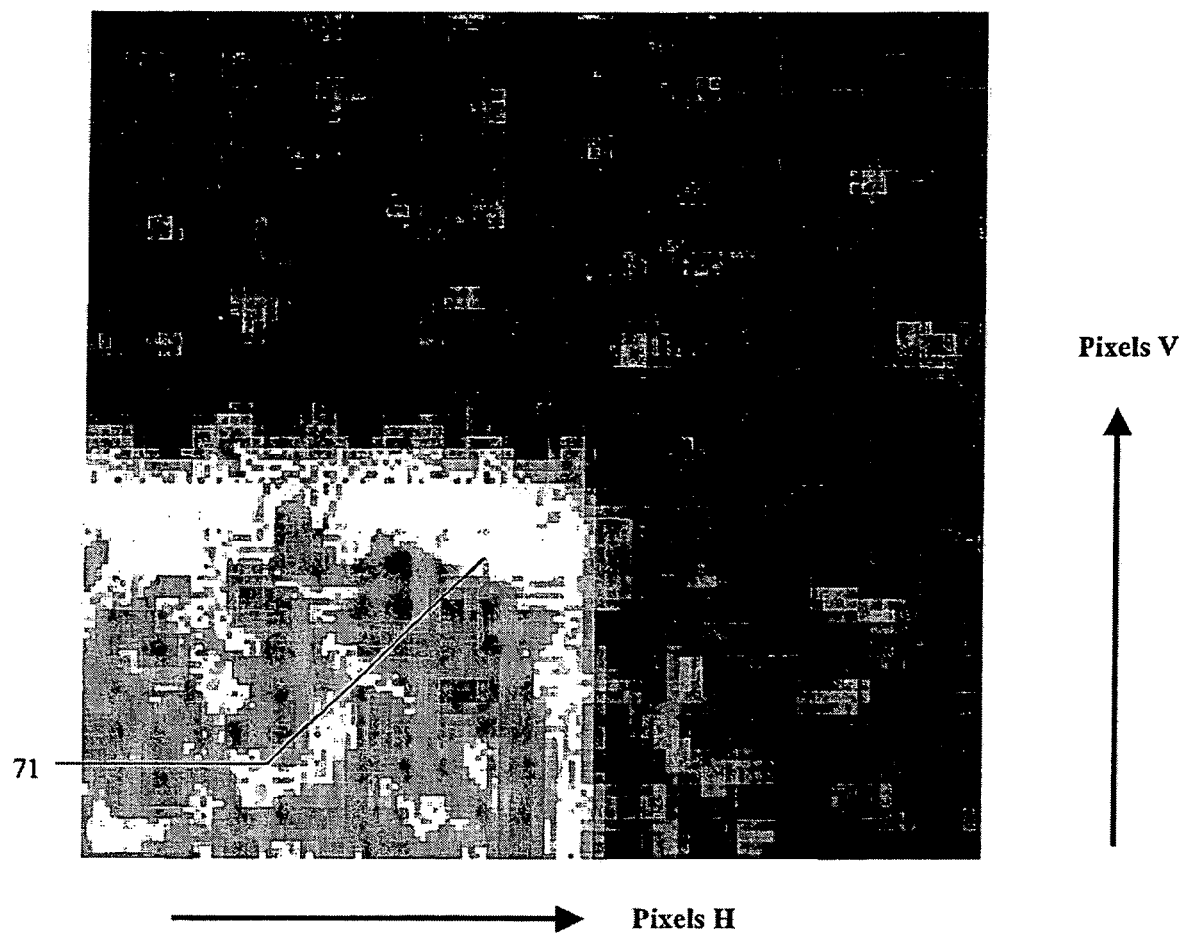
FIG. 11 is an actual pixelized output signal image of a corner feature produced by the laser projector shown in FIGS. 1 and 6.

The preliminary scan begins the following way. Amplifier 205 is set at minimum gain $G_0$ through the DAC 206. The laser beam is steered by the galvanometer 203 (mirror 5) with constant velocity and varying azimuth angle H along the trace line 73. At the end of the line 73 the galvanometer 203 stops, and the galvanometer 204 steers the beam varying elevation angle V along the short path 74. Then the galvanometer 204 stops, and the galvanometer 203 steers the beam along the retrace line 75. The scan process continues in this bi-directional manner covering the whole area that was outlined at step 51 by the scan box 70. During each trace and retrace the galvanometer 203 is driven by the stream of digital commands at equal time increments from computer 200 through the DAC 201. At each time increment computer 200 reads the output of ADC 207, thus sampling the amplified optical feedback signal. In other words, at this step, the laser projector operates in a manner such as that of a digitizing scanner. Computer 200 constructs a 2-dimensional image array row after row, and each row represents digitized optical signal along a trace or retrace scan line. As the result of this scanning, the computer 200 captures a digital "pixelized" image of the feature 71, with horizontal pixels representing sampling in azimuth angle H, and vertical pixels representing sampling in elevation angle V. An example of the "pixelized" image of the corner feature 71 is shown in FIG. 11. It should be understood the metric of the digital image captured by the laser projector is in angular units (radians or degrees).

After completion of preliminary scan, computer 200 analyzes captured digital image and determines the maximum value in the image array. That value corresponds the maximum amplitude of the amplified optical signal $S_{max}$. Then the proper amplifier gain G needed for the final scan is calculated:

$$G = \frac{U}{S_{MAX}} \quad (1)$$

where U is the input range for the ADC 207.

Next, the amplifier 205 is set to the gain G by computer 200 through the DAC 206, and the final scan begins.

Figure 10:
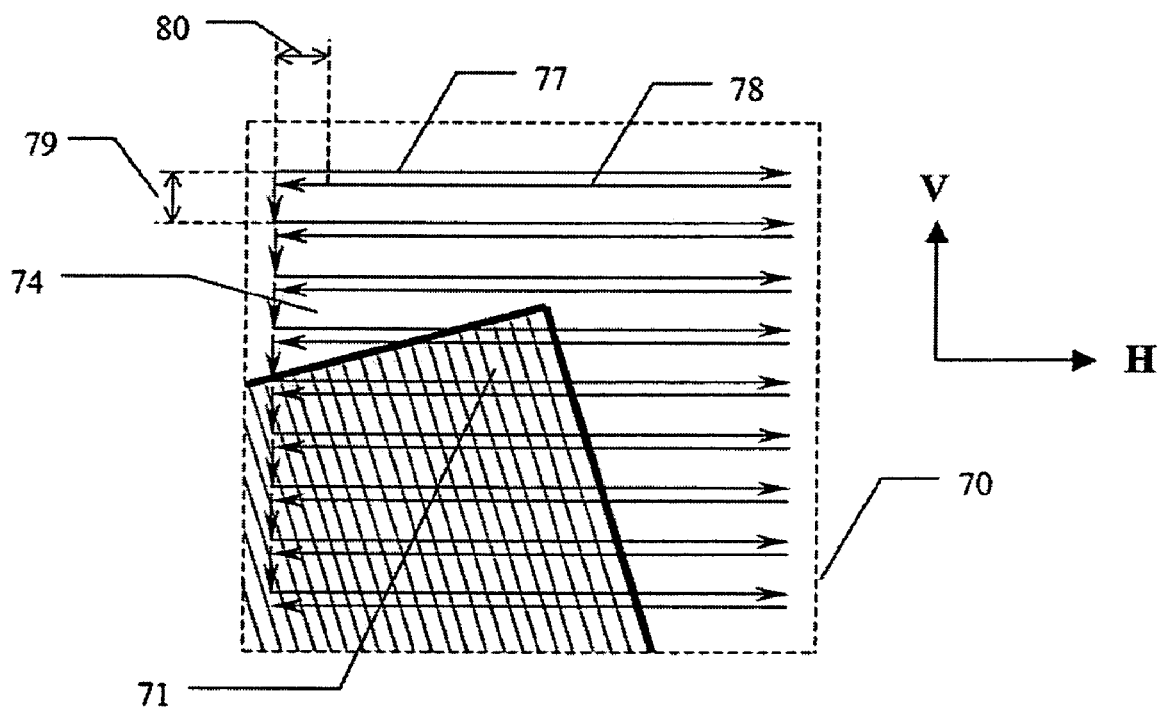

Final scan trajectory is shown in FIG. 10. It follows the bi-directional scan pattern 74. In contrast to the preliminary scan, the final scan trajectory has trace 77 and retrace 78 paths superimposed exactly on the same line (they are shown in FIG. 10 as slightly separated in the vertical direction only for illustration purpose). Otherwise, the process of final scan, galvanometer control, and the optical feedback signal digitizing are the same as described above for preliminary scan. The final scan resolution has to be adequate for the required feature location precision. Typical scan line separation 79 (V pixel size) and the sampling interval 80 (H pixel size) are each 30 to 50 micro radians.

The final scan pattern is a significant aspect of this invention. When computer 200 drives galvanometer 203 quickly, there is a noticeable lag in the ability of the galvanometer to follow the driving command. The difference between the actual and the commanded position of the galvanometer at the moment of sampling the optical signal brings an offset error to the digitized data. In other words, the output electrical signal representative of the intensity of the feedback light diffusely reflected from a point on the object is not precisely correlated with that point. The data acquired during trace scans is shifted to the left, and the data acquired during retrace scans is shifted to the right. If scan velocity is constant, the offset value is also constant. Actually, the offset value depends not only on the galvanometer lag, but also on the delay in the amplifier 205. Because the lag and delay values are usually unknown, so is the amount of the data offset. However, the absolute value of the offset is the same for trace and retrace—only the sign is opposite. Based on that, the problem of an unknown scan lag is solved in this invention by constructing separately two digital image arrays for all traces and all retraces. Computer 200 constructs each image array in the same manner as described above for the preliminary scan. Therefore, as a result of the final scan, two digital images of the feature are captured by computer 200—a "trace image" and a "retrace image".

Figure 12A:
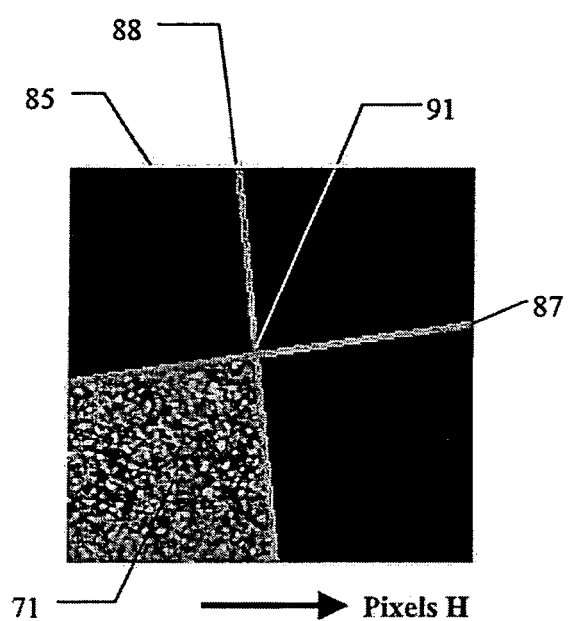
FIGS. 12A and 12B show actual pixelized output signal images of the same corner feature taken in opposite horizontal directions in a raster scan of the type shown in FIG. 10.
Figure 12B:
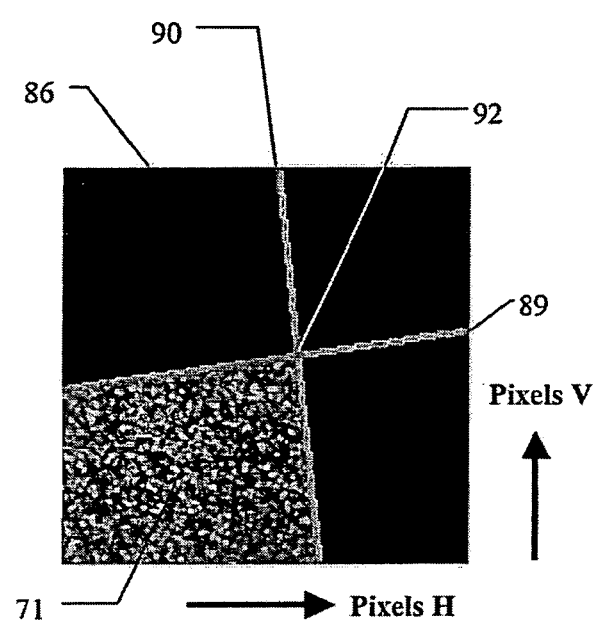

Trace and retrace digital images of the scanned corner feature 71 are shown in FIG. 12. It can be seen that the trace image 85 and the retrace image 86 look the same with exception of some offset between them in horizontal (H) direction. By processing those images separately and finding the feature location for each of them, the real feature location may be found by averaging trace and retrace locations, thereby controlling the error introduced by unknown lag.

Referring back to FIG. 7, at step 54 computer 200 runs image processing routines, separately for trace and retrace images, to detect the scanned feature location in (H, V) space, e.g. elevation and azimuth of its reference point. As it was described above, in the case of a corner, its reference point is its vertex, whether real or virtual. In other words, the vertex location in (H, V) space corresponds the beam steering direction from the projector origin to the vertex.

As the vertex is just the point of intersection of the corner's edges, the computer 200 runs a routine to detect and locate these edges in a digital image. Known methods of digital image processing for video systems, ultrasound scanners, radars and the like are described in technical literature, for example, Gonzales, R. C. and Woods, R. E., *Digital Image Processing*, 2$^{nd}$ ed., Prentice Hall, Upper Saddle River, N.J. (2002) As will be understood by those skilled in the art, image processing can include computer routines to filter noise and speckles in the image, extract pixels that lie along edges, apply image segmentation to select the strongest edge pixels, and to run least square fit yielding final edge line locations. Also, ready-to-use software libraries implementing image processing routines that can be used within the present invention are commercially available from vendors, such as MathWorks in the U.S., or Matrox in Canada. An example of edge lines 87, 88, 89, and 90 detected by digital image processing routine at step 54 is shown in FIG. 12.

At step 55 the line intersection points 91 and 92 for trace and retrace images 85 and 86 are computed. Then the feature location reference point ($H_C$, $V_C$), in angular coordinates with respect to projector's origin, is calculated as follows:

$$H_C = \frac{H_T + H_R}{2} \quad (2)$$

$$V_C = \frac{V_T + V_R}{2} \quad (3)$$

Figure 13A:
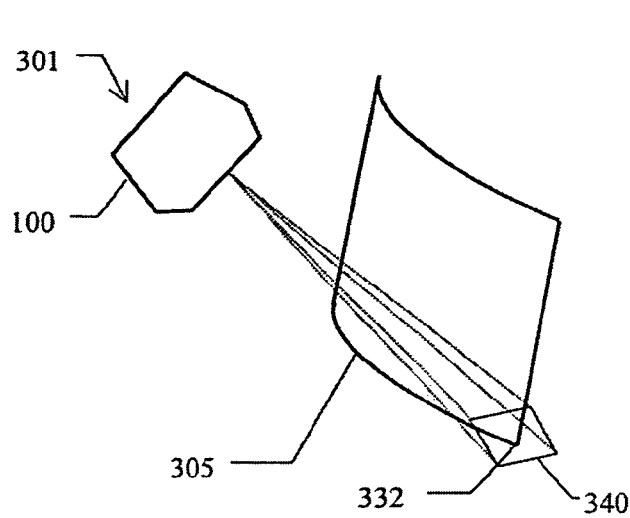
FIGS. 13A and 13B are views of a laser projector according to the present invention operated to detect a corner feature from two different angles with respect to the same object.
Figure 13C:
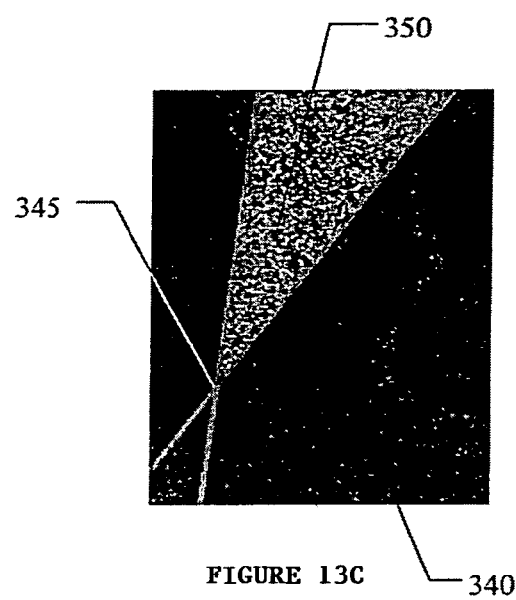
FIGS. 13C and 13D are actual output signal image of the corner feature produced by the operation of the laser projectors shown in FIGS. 13A and 13B, respectively.
Figure 13B:
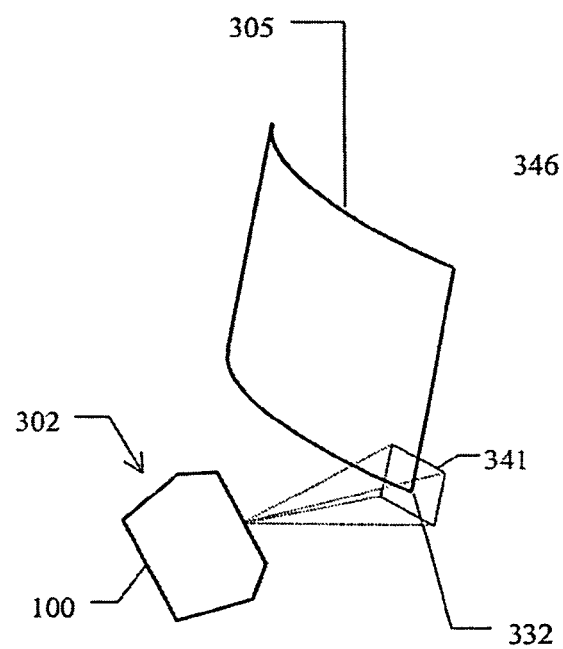
Figure 13D:
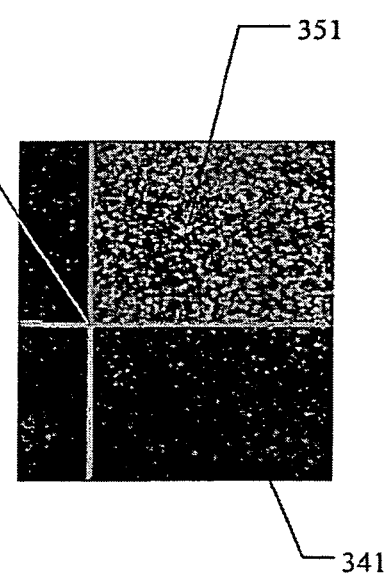

Where:
- $H_T$ and $V_T$ are the beam steering angles, azimuth and elevation, of the intersection point 91 (edge lines 87 and 88) found for the trace (T) image;
- $H_R$ and $V_R$ are the beam steering angles, azimuth and elevation, of the intersection point 92 (edge lines 89 and 90) found for the re-trace (R) image;

As mentioned above, the features are represented in the tool data set as single reference points. A shape of a feature preferably used in this invention has to provide unambiguous detection of its reference point independently of the orientation of the projector 100 with respect to the object in 3D space. An example of a preferred feature shape is a corner. The combination of the scan and image processing methods described for steps 53-54 brings an important performance advantage—the computed intersection point derived from detected edges always corresponds to the vertex of the corner feature, regardless of the projector orientation with respect to the object. This is illustrated in FIGS. 13A and 13B. When laser projector 100 is oriented in position 301 with respect to the object 305 (FIG. 13A) it scans the area 340. In this situation, the detected edges in the scanned image 350 of the corner 332, as shown in FIG. 13C, appear to for an acute angle with respect to each other. When laser projector 100 is oriented in position 302 with respect to the object 305 (FIG. 13B) it scans the area 341. For this orientation, the detected edges in the scanned image 351 of the corner 332, as shown in FIG. 13D, appears to form a right angle with respect to each other. But in both layouts the intersection points 345 and 346 unambiguously correspond to the vertex of the corner 332, and the computed angular coordinates ($H_C$, $V_C$) will be consistent in both cases with beam steering direction from the projector's origin to the vertex of the corner feature in 3D space.

Figure 14A:
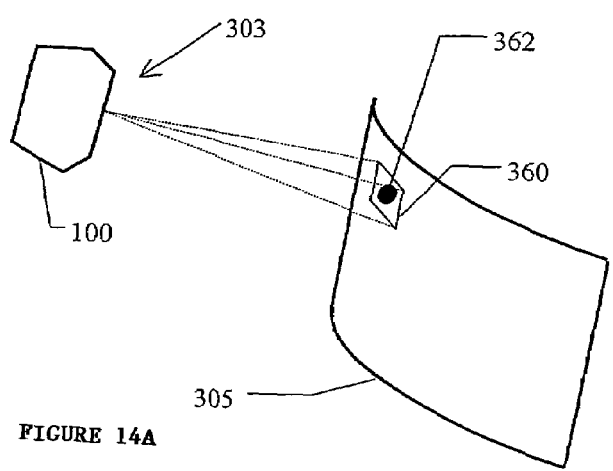
FIG. 14A is a view corresponding to FIGS. 13A and 13B showing a circular hole ("dot") object feature within the object.
Figure 14B:
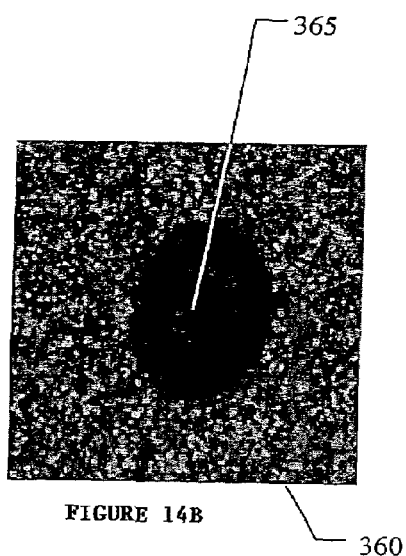
FIGS. 14B-D are views corresponding to FIGS. 13C and 13D showing the circular dot feature as imaged by the laser system of the present invention, including a scan box (FIG. 14B), a feature edge detected (FIG. 14C), and a center reference point established (FIG. 14D)
Figure 14C:
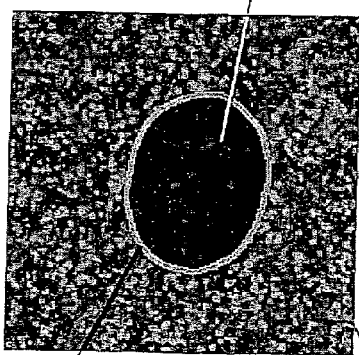
Figure 14D:
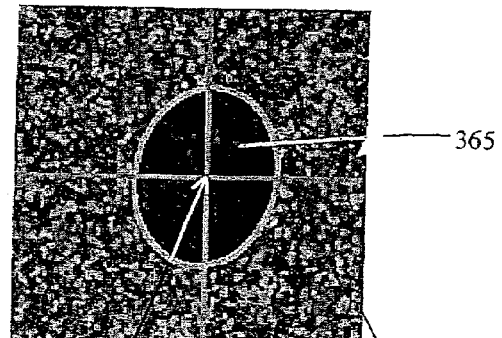

Another example of a preferred feature shape in this invention is a circular "dot". This shape is characteristic of a wide class of features such as drilled holes, fasteners, etc. Scan and image processing of a dot feature is illustrated in FIGS. 14A-14D. The laser projector 100 is oriented in position 303 with respect to the object 305, as shown in FIG. 14A. It scans the area 360 and captures the digital scan image 365 of the circular dot feature 362. The reference (fiducial) point of the circular dot feature is its center. A dot feature can be included in the Tool Data Set by specifying its center coordinates (x, y, z) with respect to the object coordinate system. As it shown in FIGS. 14B-14D, the shape of the real digital image 365 appears as elliptical for this particular orientation of the laser projector 100 with respect to the object 305. The computer 200 runs a routine to detect the edge 366 of the dot image 365 (FIG. 14C) and to find the center 367 (FIG. 14D). Again, elliptical edge detection and center finding algorithms are well known in the art, and the software libraries implementing required routines are available from Mathworks, Matrox, and other image processing software vendors. The preferred method of separate trace and retrace image processing described above for corners is also fully applicable to dot feature images. The dot feature location point ($H_C$, $V_C$) in angular coordinates with respect to projector's origin can be calculated by averaging trace and retrace image centers similarly to corner's computation using formulas (2). Different projector positions and orientations will result in different ellipticity and orientation of the image 365, but the center of the ellipse will always correspond to the center point of the dot 362, and the computed angular coordinates ($H_C$, $V_C$) will be consistent with beam steering direction from the projector's origin to the center of the dot feature in 3D space.

Referring again to FIG. 7, at step 56 the computer 200 checks if the feature scanned is the last feature in the Tool Data Set list. If it is not, a scan box for the next feature is projected at step 57, and the algorithm returns to step 52. If the last feature in the Tool Data Set has been scanned and processed, the system is ready to complete "bucking in" by finally computing projector's location and orientation in 3D space with respect to the object. At this point computer 200 accumulates a list of angular coordinates for all scanned features:

$H_1$, $V_1$;
$H_2$, $V_2$;
$H_3$, $V_3$;
... [Etc.] ...

The preferred types of features applicable to this invention are not limited by flat corners and dots described above. It should be understood that other features such as 3D corners, 2D and 3D rounded corners, fabricated countersink holes, crosses, square and diamond shaped fasteners, etc. can be used.

At step 58 the set of all computed angles and x. y, z points for the features are used by the computer 200 as data to solve a system of non-linear beam steering equations to compute the location and orientation in 3D space of the laser projector 100 with respect to the coordinate frame of the object (e.g. tool) being scanned. As is well known, there are six projector location and orientation parameters to be computed:

PX, x-coordinate of the projector origin;
PY, y-coordinate of the projector origin;
PZ, z-coordinate of the projector origin;
$\omega$, pitch—projector's rotation around the axis parallel to the X axis of the tool frame and going through projector origin;
$\phi$, yaw—projector's rotation around once rotated Y axis;
$\kappa$, roll—projector's rotation around twice rotated Z axis;

Each reference point is associated with two beam steering equations that, in generic form, can be expressed as follows:

$$F(H,V,x,y,z,PX,PY,PZ,\omega,\phi,\kappa)=0; \quad (3)$$

$$G(H,V,x,y,z,PX,PY,PZ,\omega,\phi,\kappa)=0; \quad (4)$$

Where functions F and G, as is well known, are defined by geometry of the beam steering mirror system.

At least three reference points are needed to generate at least six equations in order to compute six unknown parameters (PX, PY, PZ, $\omega$, $\phi$, $\kappa$) of projector location and orientation. With more than three reference points the system of equations becomes over-determined and has to be solved using a least-squares method. Suitable particular expressions for the laser projector beam steering equations and solving algorithms are described in detail in the aforementioned U.S. Pat. No. 6,547,397 to Kaufman and Savikovsky, the disclosure of which is incorporated herein by reference.

Once the laser projector's location and orientation in 3D space with respect to the object coordinate frame has been determined, it is ready to project glowing templates on the surface of the object following input CAD data in the form of (x, y, z) list of trajectory points defined in the object coordinate frame. A detailed description of the algorithms used in projector's computer to implement proper projection of glowing templates in 3D space is also given in U.S. Pat. No. 6,547,397.

Figure 15:
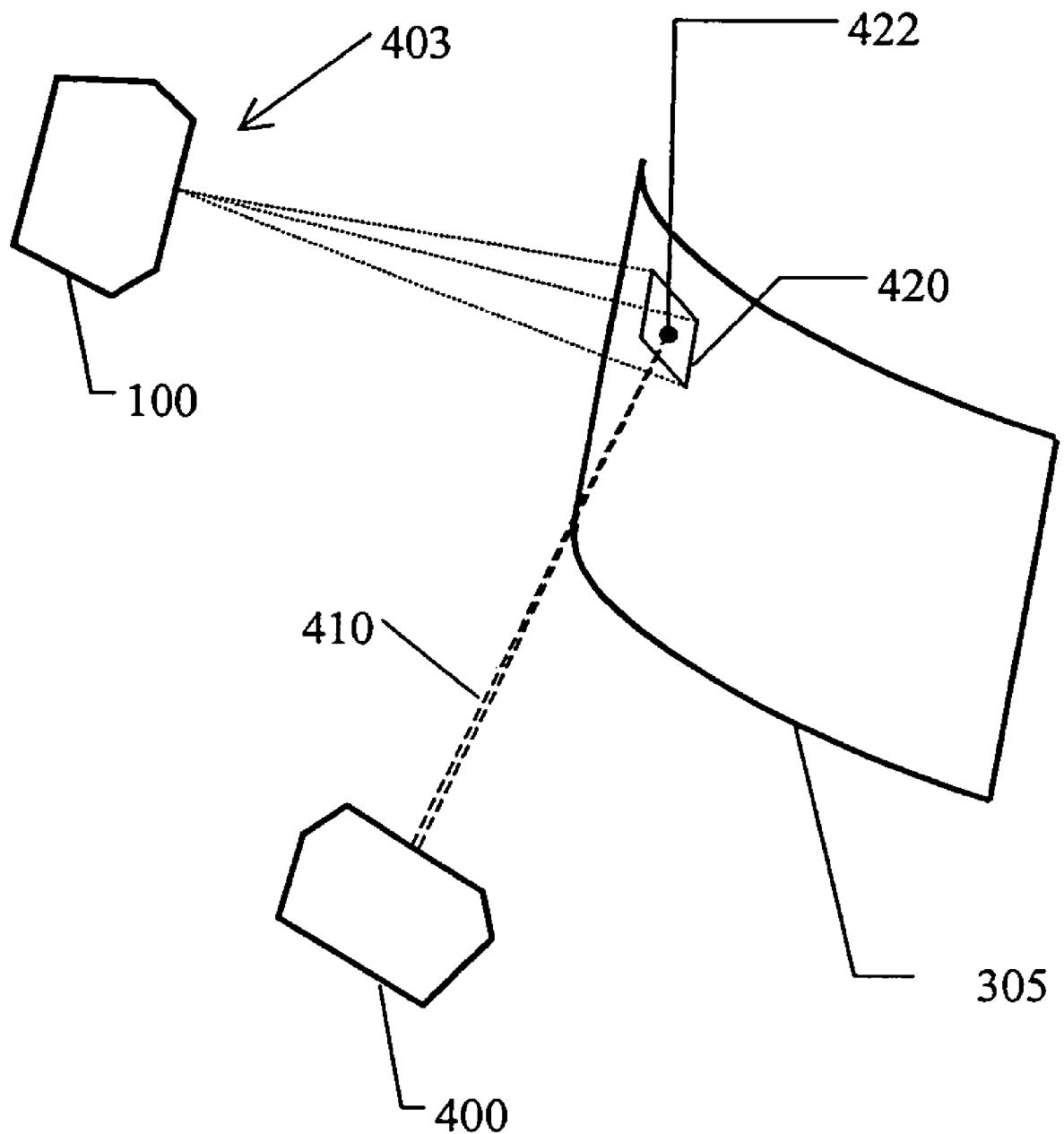
FIG. 15 illustrates an alternative method of operation of the invention where a laser spot on an object constitutes the object feature being scanned by the laser projector of the present invention.

Another aspect of this invention is the ability of the targetless laser projector 100 to detect a light spot on an object from another laser source very much the same way it detects a feature of the object. In the exemplary illustration of the embodiment of the invention shown in FIG. 15, an external source 400 directs a laser beam 401 toward the object 305. The laser beam 410 has the same wavelength as the laser wavelength used by the projector 100, preferably green light, 532 nanometers. The laser beam 410 is focused into a static spot 422 on the surface of the object 305. The diameter of the spot 422 is preferably about the same as the diameter of the focused spot that can be produced by the laser projector 100, typically about 0.4-1 mm. The power of the beam 410 is not more than 5 milliwatts to meet safety standards.

As described above, the laser projector 100 is capable of detecting very low level of light as an optical signal reflected from a diffusive surface. The projector 100 scans the area outlined by scan box 420 that contains the spot 422. Using image processing method described above for a dot feature, the projector's computer 200 locates angular coordinates (H, V) for the spot 422. Any appropriate laser system can be used as a source 400, for example, another laser projector, or simply a statically mounted laser with proper power, wavelength, and spot size on the object.

It is also contemplated that the feature detection, reference point determination, processing verification, reverse engineering, and other features and applications of this invention can be combined or enhanced with laser ranging, e.g. within the laser projector 100. As noted above, a laser projector with a high precision laser range detector is described in the Kaufman and Savikovsky '397 patent.

While the invention has been described with reference to the foregoing exemplary embodiments, and certain presently preferred features and embodiments, it will be understood that various modifications and alterations will occur to those skilled in the art from the foregoing detailed description and the accompanying drawings. For example, other known lasers, light suppression implementations, light detectors and electronic signal control and processing can be used. Available photodiodes can be used as a detector. Various other light absorbing materials and arrangements can be used in the projector to control stray scattered light. The spatial filter can take different forms, e.g. assume a different shape or use an opening with a different size relationship to the focused return beam. For example, the focal point of the converging lens for the feedback beam and/or the position of the spatial filter along the optical axis can be adjusted in conjunction with changes in the focus of the output beam to allow the use of a smaller diameter opening that blocks more of the incident stray scattered light. As noted above, the spectral filter mirror can be replaced by band pass filters in the feedback beam path after decoupling from the shared output beam path. Further, while a raster scan of object features is described, other scan patterns and techniques are known and could be used. Still further, while use of the TLP for assembly and assembly verification are described, it will be understood that the invention can be used to guide and verify fabrication steps, including painting and related masking, and the application of numbers, letters and designs whether by painting, related masking, application of decals, or otherwise, as well as fabrication steps involving material processing such as drilled holes and cut edges. It is also contemplated that the feature detection of the present invention can be used for identification, and security applications such as scanning of fingerprints or body parts.

These and other modification and alterations will be apparent to those skilled in the art and are intended to fall within the scope of the appended claims.

What is claimed is:

1. A laser projection system with feature detection on the surface of an object, comprising:

a laser projector that projects a laser light beam on the surface and scans the output beam along a beam path over the surface where a portion of said output light is reflected from the surface back to said projector as a feedback light beam, an optical detector at said projector that receives said feedback light beam and converts it into a digital image that corresponds to the detected feedback light, and a suppression system that substantially eliminates stray light, including internally scattered light, other than said feedback light from reaching said optical detector, said projected light beam and said feedback light beam associated with a given point on the surface propagating in opposite directions along said beam path.

2. The laser light projection system of claim 1 wherein said suppression system comprises a beam splitter located in said beam path that decouples said output light beam from said feedback light beam.

3. The laser light projection system of claim 2 wherein said suppression system further comprises a light dump that eliminates the split portion of said output light beam that is reflected from said beam splitter and not projected onto the surface.

4. The laser light projection system of claim 3 wherein said light dump comprises a light absorbing member located and oriented with respect to said split beam portion and said splitter to produce said split light elimination.

5. The laser light projection system of claim 3 wherein said suppression system further comprises a spectral filter acting in cooperation with said beam splitter that passes light of a selected wavelength to said optical detector.

6. The laser light projection system of claim 3 wherein said spectral filter comprises a band-pass mirror that reflects light at the wavelength of the light produced by said laser projector.

7. The laser light projection system of any one of claims 2-6 wherein said light suppression system further comprises a spatial light filter that admits said feedback light beam to said photodetector while substantially blocking stray light.

8. The laser light projection system of claim 7 wherein said spatial filter comprises a light mask with central opening aligned with said optical detector and a converging lens that brings said feedback light beam to a focus at said central opening.

9. The laser projection system of claim 8 wherein said opening is generally circular and has a diameter about four times the diameter of said focused feedback light beam.

10. The laser projection system of claim 1 further comprising a computer that controls said scanning and processes said digital image.

11. The laser projection system of claim 10 wherein said computer coordinates said digital image of a given point on said surface with a given beam direction, and therefore an associated location on said surface, by correcting for delays in the implementation of beam scan instructions from said computer to said projector and for delays in the detection and processing of the detected digital image.

12. The laser projection system of claim 10 wherein said computer directs said scanning to produce a scan box glowing template that encloses feature points on the surface.

13. The laser projection system of claim 12 wherein said computer further operates to scan the surface outlined by the scan box.

14. The laser projection system of claim 13 wherein said computer further operates to calculate a fiducial point from the resulting digital image from the feedback beam.

15. The laser projection system of claim 11 wherein said computer controls said scanning as a raster scanning over a selected portion of said surface containing a feature and corrects for lag in said scanning by directing coincident trace and retrace scans, forming trace and re-trace images, and averaging them.

16. The laser projection system of claim 1 wherein said reflected light beam is diffusely reflected and has a power level of about 50 to about 500 picowatts.

17. The laser projection system of claim 1 further comprising a second light source that projects a light spot on the object that is a feature.

18. A method for assembling with precision placement component parts and fabrication processing in 3D space, onto and/or supported by and object, comprising,
projecting a scanned laser light beam onto the object,
selecting features on the object before assembly, said selecting including creating a scan box around a selected feature,
scanning said projected light beam within the scan box,
detecting light diffusely reflected back from said object along said scanned laser light beam,
suppressing stray light, including internally scattered light produced by said projecting or scanning, from entering the detector except for said feedback light,
creating a digital image of said features from said detected feedback light,
calculating fiducial points from said features,
calculating from plural fiducial points on the object the relative position and orientation of the source of said projecting and said object, and
projecting a glowing template on the object that guides the assembly of the parts or fabrication processing on or to the object.

19. The process of claim 18 further comprising acquiring at least one feature on the object surface that serves as a fiducial point.

20. The feature detection process of claim 19 wherein the intensity of said feedback light beam from said surface is in the range of 50 to 500 picowatts.

21. The feature detection process of claim 19 further comprising coordinating said scanning with said acquisition to accommodate for mechanical and signal processing delays and accurately associate a given one of said scanned points on the surface with a given digital image.

22. The feature detection process of claim 19 wherein said fiducial point acquisition comprises projecting a glowing template to form a scan box around a selected feature point, and scanning said output laser beam over the portion of the surface within said scan box.

23. The feature detection process of claim 22 where scanning within said scan box is a raster scanning, first in a preliminary mode to set at least one operating parameter of said detecting, and then in a final mode to acquire the features of the surface, and calculating said fiducial point from the acquired features.

24. The feature detection process of claim 19 wherein said detecting includes suppressing stray light, including internally scattered light produced by said projecting or scanning, other than said feedback beam from being detected.

25. The feature detection process of claim 24 wherein said suppressing comprises splitting both the output and feedback light beams, and suppressing the split portion of said output light beam that is not projected onto the surface.

26. The feature detection process of claim 25 wherein said suppressing further comprises spectrally filtering a split portion of said feedback beam before said detecting of it, and spatially filtering said detecting from all light except that of said split, spectrally-filtered, feedback beam.

* * * * *